(12) United States Patent
Monti (10) Patent No.: US 10,379,062 B2
(45) Date of Patent: Aug. 13, 2019

(54) DETECTION SYSTEM FOR DETECTING AND DETERMINING AN INTEGRITY OF PHARMACEUTICAL/PARAPHARMACEUTICAL ARTICLES

(71) Applicant: MARCHESINI GROUP S.p.A., Pianoro (Bologna) (IT)

(72) Inventor: Giuseppe Monti, Pianoro (IT)

(73) Assignee: MARCHESINI GROUP S.P.A., Pianoro (Bologna) (IT)

(*) Notice: Subject to any disclaimer, the term of this patent is extended or adjusted under 35 U.S.C. 154(b) by 190 days.

(21) Appl. No.: 15/548,363

(22) PCT Filed: Feb. 16, 2016

(86) PCT No.: PCT/IB2016/050809
§ 371 (c)(1),
(2) Date: Aug. 2, 2017

(87) PCT Pub. No.: WO2016/132281
PCT Pub. Date: Aug. 25, 2016

(65) Prior Publication Data
US 2018/0017506 A1    Jan. 18, 2018

(30) Foreign Application Priority Data
Feb. 19, 2015    (IT) .............................. BO2015A0083

(51) Int. Cl.
*G06K 9/00* (2006.01)
*G01N 21/95* (2006.01)
(Continued)

(52) U.S. Cl.
CPC ......... *G01N 21/9508* (2013.01); *B65B 5/103* (2013.01); *B65B 37/04* (2013.01);
(Continued)

(58) Field of Classification Search
CPC ....... B33Y 10/00; G06T 19/20; A61B 3/0025; A61B 3/0041; A61B 3/111
(Continued)

(56) References Cited

U.S. PATENT DOCUMENTS

| 4,319,269 A * | 3/1982 | Kajiura ..................... B07C 5/10 348/92 |
| 5,363,968 A * | 11/1994 | Soloman ................... B07C 5/36 198/725 |
| 2007/0289660 A1 * | 12/2007 | Aylward ................. B65B 5/103 141/18 |

FOREIGN PATENT DOCUMENTS

| EP | 2653390 A1 | 10/2013 |
| JP | 2012 086859 A | 5/2012 |
| JP | 2012 159456 A | 8/2012 |

* cited by examiner

*Primary Examiner* — Charlotte M Baker
(74) *Attorney, Agent, or Firm* — R. Neil Sudol; Henry D. Coleman (57) ABSTRACT

A detection system (S) for detecting and determining an integrity of pharmaceutical/parapharmaceutical articles includes a conveyor device (1), for conveying and advancing articles having an advancement section (10) along which the articles are advanced on a flat plane, in a line one after another in an advancement direction (A). The system (S) has a processor (E) for data processing; at least one color matrix video camera (2) for acquiring images of the articles advancing along the advancement section, a laser projector (P) able to emit and project a laser beam (L) so that the laser beam (L) crosses the advancement section (10) and a high-speed linear three-dimensional video camera (3) for acquiring the images of the cut profiles of the articles crossing the laser beam.

5 Claims, 5 Drawing Sheets

(51) Int. Cl.
*B65B 57/14* (2006.01)
*B65B 5/10* (2006.01)
*G06T 7/521* (2017.01)
*G06T 7/90* (2017.01)
*B65B 37/04* (2006.01)
*G01B 11/06* (2006.01)
*G01B 11/25* (2006.01)
*G01N 21/27* (2006.01)
*G06T 7/00* (2017.01)
*H04N 5/247* (2006.01)
*G01N 21/84* (2006.01)

(52) U.S. Cl.
CPC .......... *B65B 57/14* (2013.01); *G01B 11/0691* (2013.01); *G01B 11/25* (2013.01); *G01N 21/27* (2013.01); *G06T 7/001* (2013.01); *G06T 7/521* (2017.01); *G06T 7/90* (2017.01); *H04N 5/247* (2013.01); *G01N 2021/845* (2013.01); *G01N 2201/12* (2013.01); *G06T 2207/10024* (2013.01)

(58) Field of Classification Search
USPC ............. 382/141; 348/88, 132, 92; 356/431; 141/18
See application file for complete search history.

DETECTION SYSTEM FOR DETECTING AND DETERMINING AN INTEGRITY OF PHARMACEUTICAL/PARAPHARMACEUTICAL ARTICLES

FIELD OF THE INVENTION

The present invention relates to the technical sector concerning packaging of pharmaceutical/parapharmaceutical articles, such as for example pills, tablets, capsules, etc., in relative containers, such as for example bottles or cells of blister strips.

DESCRIPTION OF THE PRIOR ART

In this specific technical sector, when the discretepharmaceutical/parapharmaceutical articles are to be packed, such as for example, as mentioned above, pills, tablets, capsules, etc., inside containers, such as for example bottles or cells of blister strips, it is of fundamental importance to be able to first perform a recognition of the integrity and suitability of the articles, i.e. their exact correspondence, in terms of shape, dimensions, aspect and colour, with the predetermined and determined type of article that is to be packed, before the articles reach the infeed/packaging zone, where the articles are then directed into the containers.

It is in fact necessary to prevent the articles (tablets, pills, capsules) that are not entirely integral, i.e. those articles which are partly damaged or scratched or broken, or those articles that are not suitable, i.e. which do not correspond in terms of shape or colour, to the predetermined and prefixed type of article which is to be packed, i.e. those articles which, though integral, have a shape and/or colour different to the predetermined ones for the predetermined article, from being erroneously inserted in the containers which will then be put up for sale.

The possibility of being able to perform these controls, i.e. carrying out a validating operation, of the integrity of the article and its correspondence in terms of shape and colour to the predetermined one, before the article is introduced into a relative container, can in fact enable a discriminatory choice, i.e. the ability to distinguish if an article is suitable or not for being inserted into the container, and therefore can perform an operation of rejecting the article before it can be directed towards the infeeding/inserting station of the articles into the containers.

At present various detecting systems are known and used for acquiring information on the shape and appearance of the articles so as to detect and determine whether these articles are integral or not, suitable or not and corresponding to the predetermined type of articles that must be inserted and packed internally of the relative container (bottle, cells of blister strips and so on).

A first known system involves the exclusive use of optic sensors, such as video cameras, for acquiring the image of an article in motion.

In these systems, the articles to be validated are usually distanced from one another and a video camera is positioned such that the lens thereof is facing towards the advancement pathway of the articles.

For example, the articles are distanced and are advanced along an inclined conveyor or are dropped by gravity towards an underlying container to be filled or a temporary storage hopper.

In this way the video camera can capture images of each article transiting across the visual field of the relative lens: consequently the video camera will provide an image from which, via a control board connected to the video camera, it is possible to collect information on the shape, appearance and colour of the article and to compare it with the corresponding information for an integral article and corresponding to the prefixed type of article to be packed.

This system however has a series of drawbacks.

In fact, the video camera can capture an image only of the portion or part of the article facing toward the lens of the video camera, so it will only be possible to obtain a flat image in 2D (two dimensions, width and length), i.e. an image of the outline, in plan view, of the article and its appearance internally of this outline (i.e. if there are imperfections internally of the outline of the article facing towards the video camera).

With this type of detecting system, therefore, it is not possible to collect information on the effective thickness and three-dimensional profile which the article transiting across the field of action of the videocamera lens might have.

Therefore articles having a same outline but a different thickness and three-dimensional profile are classified as articles of the same type.

Therefore, in a case in which the shape of the outline captured by the video camera corresponds to the outline of the suitable reference article, those articles will all be indicated as valid, even if only some of them (or none of them) effectively have a thickness and three-dimensional profile corresponding to that of the suitable reference article.

Consequently, with the use of the detecting systems it is not possible to have the certainty that the articles indicated as valid are effectively all valid, integral and corresponding (in terms of thickness and three-dimensional profile) to the type of predetermined article to be packed, so that there can be bottles or blister packs containing articles not corresponding to the predetermined type of article to be packed.

The detecting systems exclusively using video cameras, while on the one hand providing immediate visual information on the shape of the outline and the colour of the articles, are not definitively able to supply precise and meaningful information on the effective shape of the thickness dimension and three-dimensional profile thereof.

A further system of known type for detecting the integrity of pharmaceutical/parapharmaceutical articles uses impedance sensors, in particular capacitive sensors, such as capacitors, which are positioned with the armatures facing one another so as to be located in a transit position of the articles which are to be verified.

In some of these systems, such as for example the one described in document US2009/056825, the articles are made to drop by force of gravity, and therefore the capacitor is arranged in such a way that the two armatures are located along the falling pathway of the articles, in particular in such a way that the falling articles pass between the two armatures.

In this way, for each falling passage of an article between the two armatures of the capacitor, the signal emitted by the capacitor will be indicative of the shape of the transited article: this signal is compared with reference values for evaluating whether the article is integral or not and in compliance with the requested parameters.

In other systems, in which the articles are to be advanced along a V-shaped inclined conveyor, such as for example in document EP 2.048.082, the capacitor is predisposed so that the two armatures are facing and parallel to the two lateral walls of the V-shaped inclined conveyor, and so that the two armatures are connected to an oscillating circuit, with one of the two armatures connected to a reference potential.

The passage of an article across the armature of the capacitor determines a variation of the dielectric constant of the dielectric across the two armatures which translates into, a disturbance in frequency of the signal in output from the oscillator circuit, for the time used by the article to cross the armatures of the capacitor.

The waveform of the output signal will be different according to the shape, dimension and mass of the article which transits between the two armatures, therefore the signal provided by a non-integral article, as it is damaged (because it is chipped, broken or scratched) will not correspond to the value of the reference signal for an integral article.

The use of these systems, which utilise capacitive sensors (capacitors) has not however provided optimal results as, firstly, are not able to supply information on the colour of the article and, secondly, the signals provided by the capacitive sensors are influenced by the way in which the article transits across the capacitor, i.e. if it is closer or not to the armature connected to the reference potential, or by the orientation with which the article transits between the two armatures.

For example, the Applicant has found that for a same article, for example an article not entirely integral, the capacitor can provide different signals according to whether the article transits closer to one armature rather than to another: for example, for an integral article, the capacitor has provided signals corresponding to the reference value for the predetermined integral article, when the article has transited across the capacitor close to the armature connected to the reference potential, while it has provided signals not corresponding to the reference value for the integral article when it has transited close to the armature of the capacitor not connected to the reference potential of the oscillator circuit.

SUMMARY OF THE INVENTION

The aim of the present invention is to provide a new detection system for detecting and determining an integrity of pharmaceutical/parapharmaceutical articles that can obviate the various drawbacks described above and present in the prior art.

In particular an aim of the present invention is to disclose a new detection system able to provide precise information on the effective integrity of the articles, relative to their appearance, shape, outline, thickness, three-dimensional profile and colour.

The system provided by the invention can be used equally either in validating and counting apparatus, which, once the system has verified the integrity of the articles, also performs the counting thereof before their inserting internally of a relative bottle, proceeding instead to the rejection of the non-integral ones or those not corresponding (in terms of appearance, shape, thickness or colour) to the predetermined type of articles, and in blister-packing machines, where, once the system has verified the integrity of the articles, the articles (i.e. the articles verified as integral) can be directed towards the infeeding station which performs the inserting thereof into the cells of a blister strip.

These aims are attained with a detecting system in accordance with claim 1.

Other advantageous characteristics of the system of the present invention are set out in the dependent claims.

BRIEF DESCRIPTION OF THE DRAWINGS

The characteristics of the detecting system for detecting and determining an integrity of pharmaceutical/parapharmaceutical articles of the present invention are described in the following with reference to the appended tables of drawings, in which.

DESCRIPTION OF THE PREFERRED EMBODIMENTS

With reference to the accompanying tables of drawings, reference (S) denotes the detecting system, for detecting and determining the integrity of pharmaceutical/parapharmaceutical articles, such as for example tablets, pills, capsules, etc.

Figure 1:
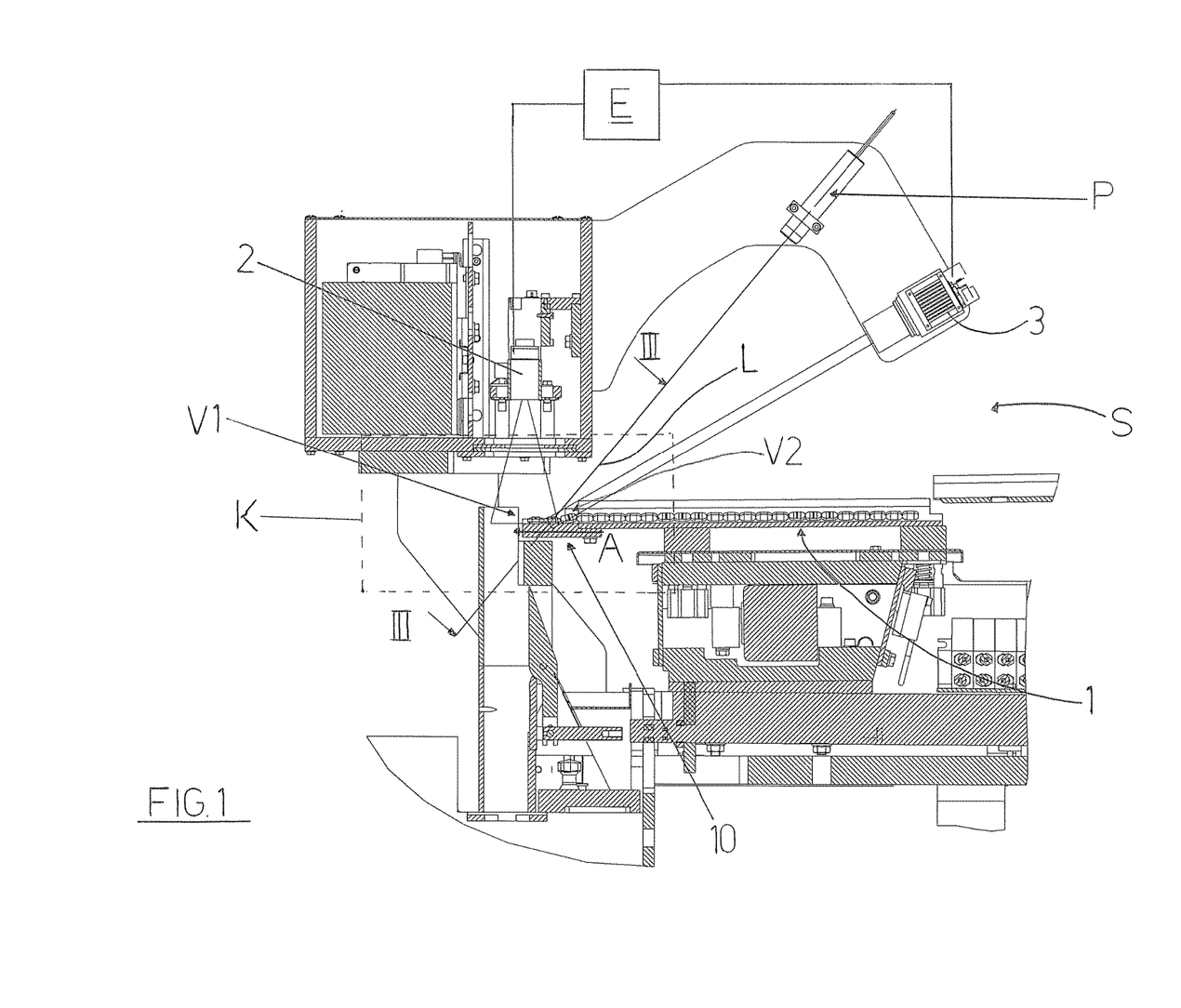
FIG. 1 is a schematic illustration according to a lateral view in section of a preferred embodiment of the detecting system of the invention.
Figure 2:
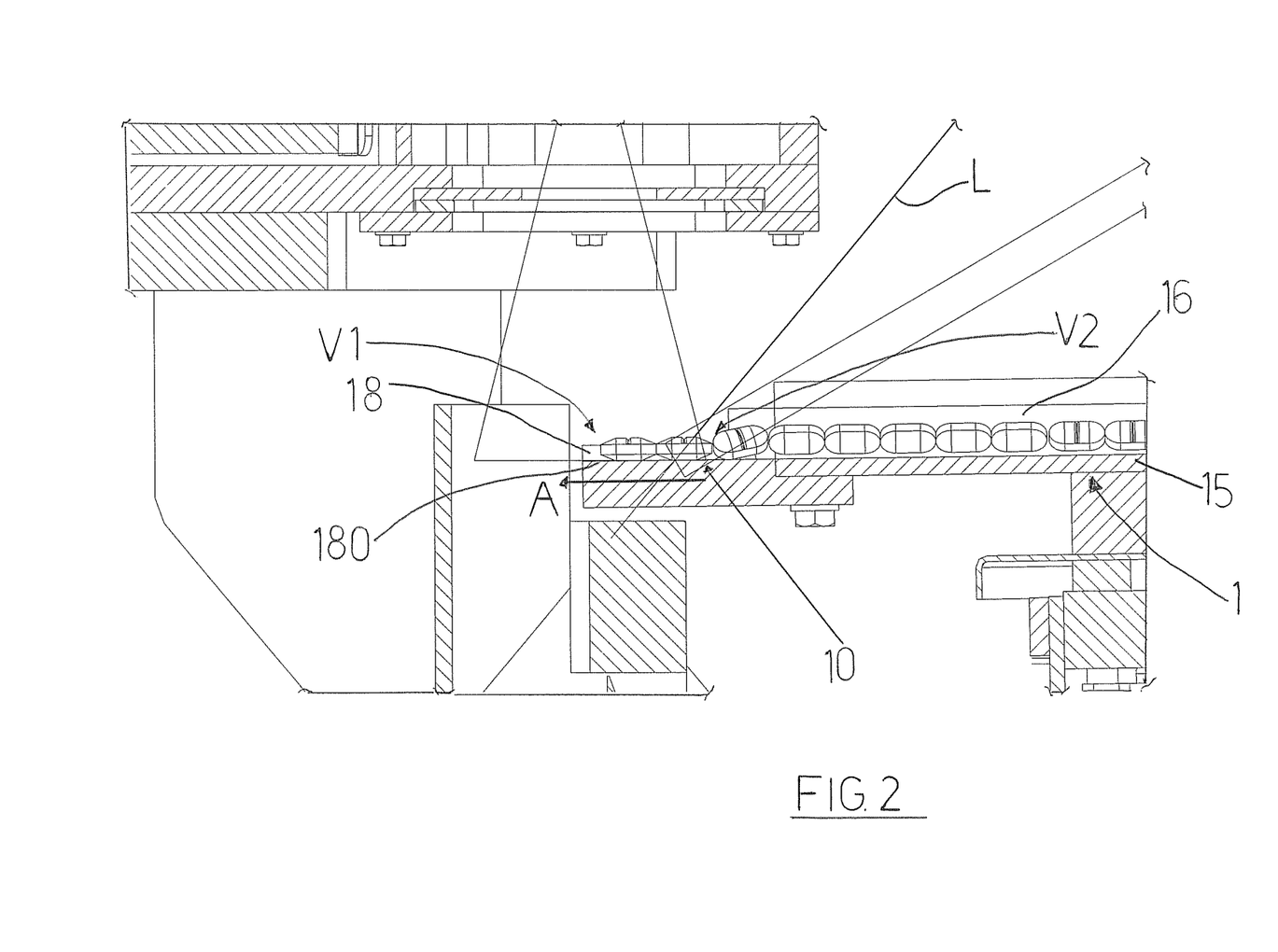
FIG. 2 is the view of detail K of FIG. 1 in a larger scale.

As illustrated for example in FIG. 1, the detecting system (S) of the invention comprises a conveyor device (1), for conveying and advancement of the articles.

For example, the conveyor device (1) can be arranged immediately downstream of a hopper in which the articles to be packed are stored or in cascade to conveyors of the articles.

The conveyor device (1) of the system (S) of the invention can be positioned, predisposed and installed, as mentioned in the foregoing, in both validating and counting apparatus, in an upstream position at which the articles are directed internally of relative bottles, or in blister machines in a position upstream of the infeeding station, where the articles are inserted singly internally of corresponding cells of a blister strip.

The conveyor device (1) comprises an advancement section (10) along which the articles to be verified are advanced on a plane in line, one after another in an advancement direction (A).

The peculiarities of the detecting system (S) of the invention consist in the fact that it comprises:
  a processor (E) for data processing;
  at least a colour matrix video camera (2), connected to the processor (E);
  a laser projector (P) able to emit and project a laser beam (L),
  a high-speed linear three-dimensional video camera (3), connected to the processor (E).

In particular, the special characteristics of the system (S) of the invention consist in the fact that, as can be clearly seen in FIG. 1, the at least a colour matrix video camera (2) is arranged above the advancement section (10) of the conveyor device (1) and is predisposed such that the relative lens is facing towards the advancement section (10) in such a way that the relative visual capturing field (V1) for acquiring the images is at the advancement section (10), across which the articles are advanced one at a time.

In this way the colour matrix video camera (2) can capture a series of images of the outline and colour of each article, during advancement thereof along the advancement section (10) across the visual field (V1) of the video camera (2).

The processor (E) is specifically programmed to receive the images acquired by the colour matrix video camera (2) and process them in such a way as to provide, for each article that has crossed the visual field (V1) of the colour matrix video camera (2) during advancement thereof along the advancement section (10), a first datum relative to the effective shape of the outline and colour of the article.

The laser projector (P) is specially positioned above the conveyor device (1) and predisposed such as to project and direct a laser beam (L) into the advancement section (10) of the articles in a position internally of the visual field (V1) of image capture of the at least a colour matrix video camera (2), in such a way that the laser beam (L) can be crossed by each of the articles advancing in a line one after another along the advancement section (10).

Further, the high-speed linear three-dimensional video camera (3) is specifically positioned and predisposed so that the lens thereof is facing towards the advancement section (10) so that the visual field (V2) thereof for capturing the images is at a zone in which the laser beam (L) is crossed by the articles advancing in a line, one after another, along the advancement section (10), internally of the visual capturing field (V1) of the at least a colour matrix video camera (2).

Figure 3:
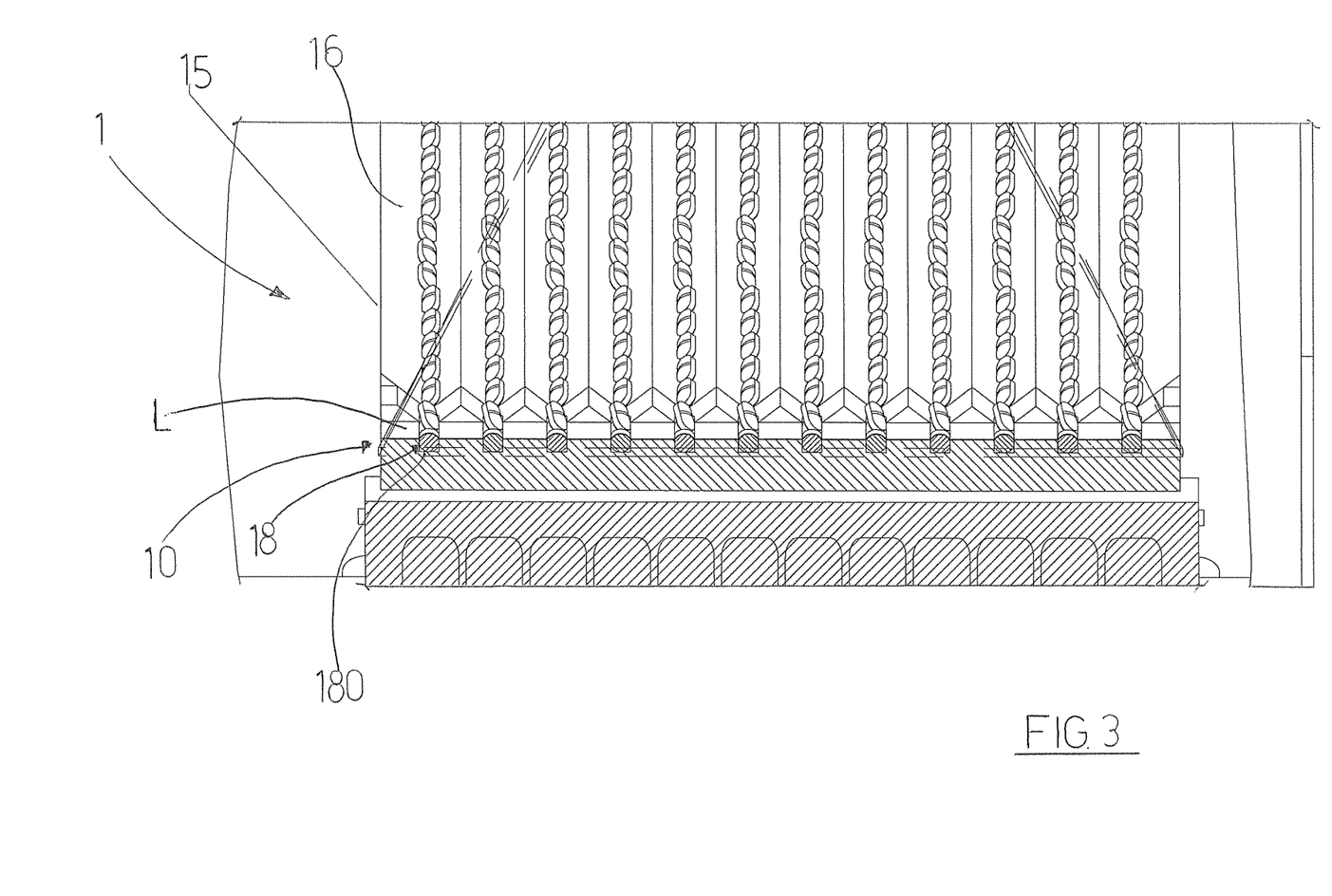
FIG. 3 is the view according to section plane illustrated in FIG. 1.

With this particular arrangement, the high-speed three-dimensional linear video camera can capture a succession of images corresponding to successive cut profiles in the laser beams (L) by each article during crossing thereof of the laser beam (L) (see for example FIG. 3 which represents the view along section plane III-III of FIG. 1, taken at the plane defined by the laser beam (L) and showing a representation of an instantaneous image of a profile cut by an article which is crossing the laser beam (L) during advancement of the article along the advancement section (10) in the advancement direction (A)).

Lastly, the processor (E) is further programmed so as:

to receive the images of the successive profiles cut in the laser beam (L) by each article, captured by the high-speed linear three-dimensional video camera (3);

to process the images so as to supply a second datum relating to the effective thickness and shape of the three-dimensional profile of each article which has crossed the laser beam (L);

to associate the second datum to the first datum concerning the outline and colour of the same article;

to process the first datum and the second datum so as to define, for each article which is transited from the advancement section (10) and which has crossed the laser beam (L), an indicative datum of the outline, colour, thickness and three-dimensional profile of the article;

to compare the indicative datum with a reference datum representative of a whole article having a predetermined outline, colour, thickness and three-dimensional profile, and consequently supply a validation or rejection notice in relation to the article.

In this way, with the detecting system (S) proposed by the invention, for each article that has passed across the laser beam (L) and which has transited across the advancement section (10) of the conveyor device (10), it is possible to obtain, with precision and certainty, information relative to the effective shape of the outline of the articles, the colour, the shape of the thickness and the shape of the three-dimensional profile and compare this information with the reference information corresponding to the integral article and of a prefixed type (in terms of outline, thickness and three-dimensional profile) which is to be packed.

In particular, this is possible due to the fact that the laser beam (L) crosses the advancement section (10) in a position internally of the visual field (V1) of the at least a colour matrix video camera (2) and the visual field (V2) of the high-speed three-dimensional linear matrix video camera (3) is at the zone in which the laser beam (L) is crossed by the articles advancing in a line, one after another, along the advancement section (10), internally of the visual capturing field (V1) of the at least a colour matrix video camera (2).

In this way, for each article that starts crossing the laser beam (L) it is possible to have both immediate images captured by the matrix video camera and images captured by the linear video camera (3): this enables the processor (E) to immediately associate the images captured by the matrix video camera (2) to those captured by the linear video camera (3) so as to process the necessary information and to have, for each article, the datum relating to the integrity or non-integrity thereof and its correspondence, or not, to the predetermined type of article which is to be packed.

Further, the detecting system (S) of the invention, for each article crossing the laser beam and transiting along the advancement section (10) of the conveyor device (1), is able to precisely acquire the information relating to the effective shape of the outline, the effective colour, the effective thickness and shape of the three-dimensional profile due to the fact that the articles are arranged in plan view on a face thereof on the advancement section (10) and in a line, one following another.

In fact, because of this specific arrangement of the articles, the at least a linear colour video camera (2) is able to capture, with the best possible definition and precision, the effective shape of the article as well as its effective real colour, as with this arrangement there is the maximum contrast between the article itself and the advancement section (i.e. between the outline of the article and the environment/zone immediately surrounding the article itself).

Therefore, with the above-described detailed peculiarities, the detecting system (S) of the invention is able to provide, for each article reaching the end of the advancement section (10) of the conveyor device:

a relative warning signal of effective integrity and suitability and enabling the validating/counting apparatus or the blister-packing machine on which it is predisposed and used to direct the article internally of a bottle or to the infeeding zone of the articles into the cells of the blister pack, or a warning signal indicating non-integrity/suitability, and therefore enable the validating/counting apparatus or the blister-packing machine a switching/reject action (for example by means of a puff of air, a mobile tab or another device) so as to deviate and convey the non-recognised article as integral/valid towards a collecting zone of the defective articles.

Other advantageous characteristics of the detecting system (S) of the present invention are described in the following.

The at least a colour matrix video camera (2) is arranged above the advancement section (10) such that the relative lens is perpendicular to the advancement section (10).

A possible preferred arrangement of the laser projector (P) can be one in which the laser projector (P) is arranged so that the laser beam (L) crosses the plane of the advancement section (10) by an angle of less than or equal to 90°.

In particular the laser beam crosses the plane at an angle preferably comprised between 90° and 40°, preferably an angle of 50°.

A preferred possible arrangement for the high-speed three-dimensional linear video camera (3) can be one in which the video camera (3) is arranged so that the axis of the relative lens forms, with the plane of the advancement section (10), an angle of less than 60°, in particular an angle comprised between 60° and 20°, preferably an angle of 30°.

The at least a colour matrix video camera (2) is a video camera having a resolution of 1280×1024 pixel, while the high-speed linear three-dimensional video camera (3) is a video camera known as a "high speed 3D camera" with a resolution of 2048×1088 pixel which supplies to the processor (E) a profile at 2048 heights on the basis of the profile cut in the laser beam (L) by the passage of an article.

The conveyor device (1) is constituted by a vibrating conveyor (15) comprising at least a V-shaped channel (18) along which the articles are advanced in an inclined configuration resting on one of the V-shaped walls, while the advancement section (10) is constituted by at least a straight channel (18) which is arranged consecutively to the V-shaped channel (16) and exhibits a flat bottom (180) on which the articles rest, and walls conformed in such as way as to be able to receive and accommodate the articles so that the articles are arranged with a face thereof resting on the flat bottom (18).

In particular, the vibrating conveyor (15) comprises switching and orientating means (4) for orientating and arranging the articles in outlet from the V-shaped channel (16) resting on a face thereof on the flat bottom (180) of the straight channel (18).

For example, the switching and orientating means (4) can be constituted by specially conformed and inclined walls arranged at the terminal zone of the V-shaped channel (16) having an extension such as to switch and direct the articles so that they change orientation by being arranged, with a face thereof, the largest face, facing downwards so that the face can go to rest on the flat bottom (180) of the straight channel (18) of the advancement section (10).

Figure 4:
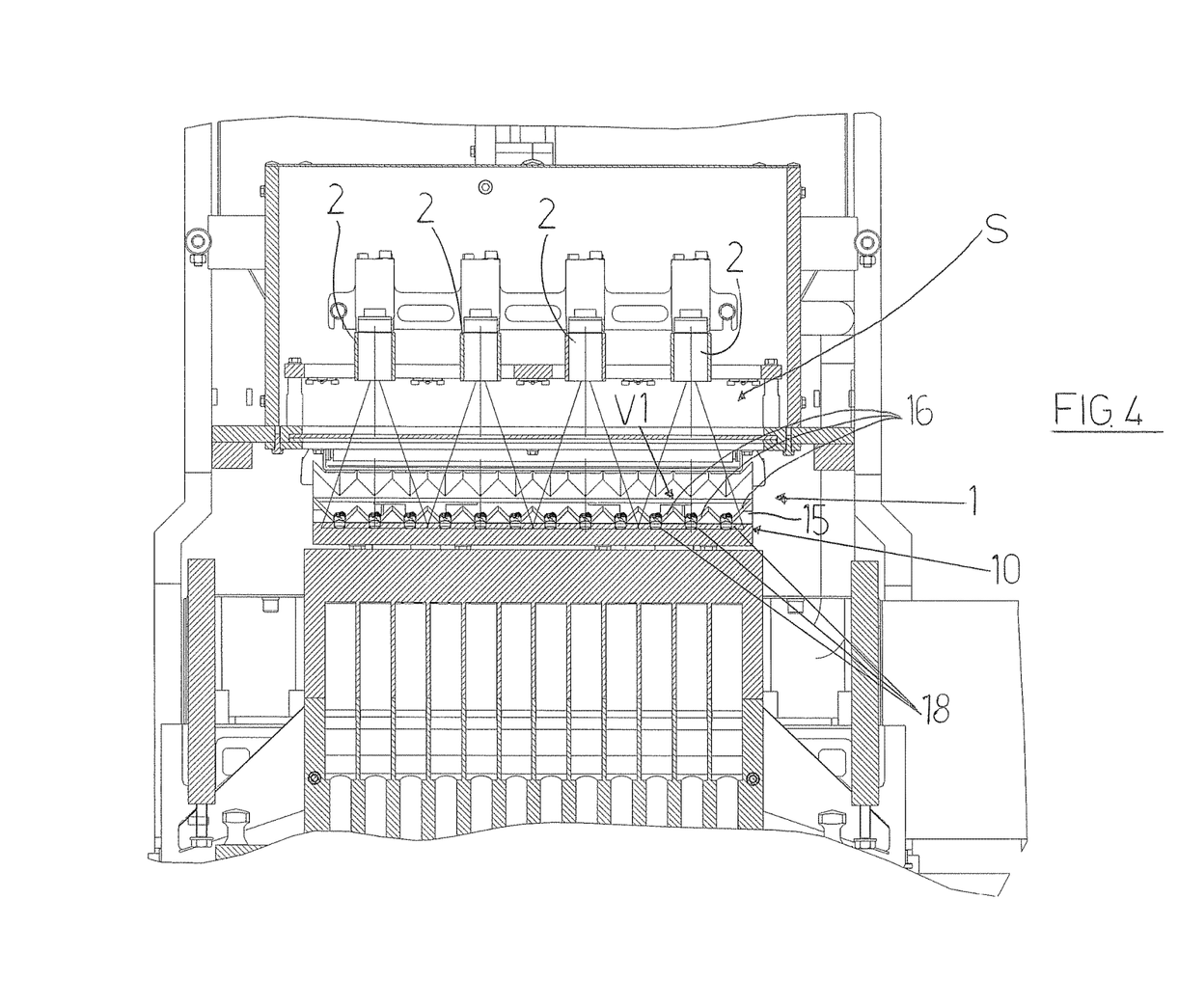
FIG. 4 is a schematic view according to a front view in section of the detecting system of FIG. 1.
Figure 5:
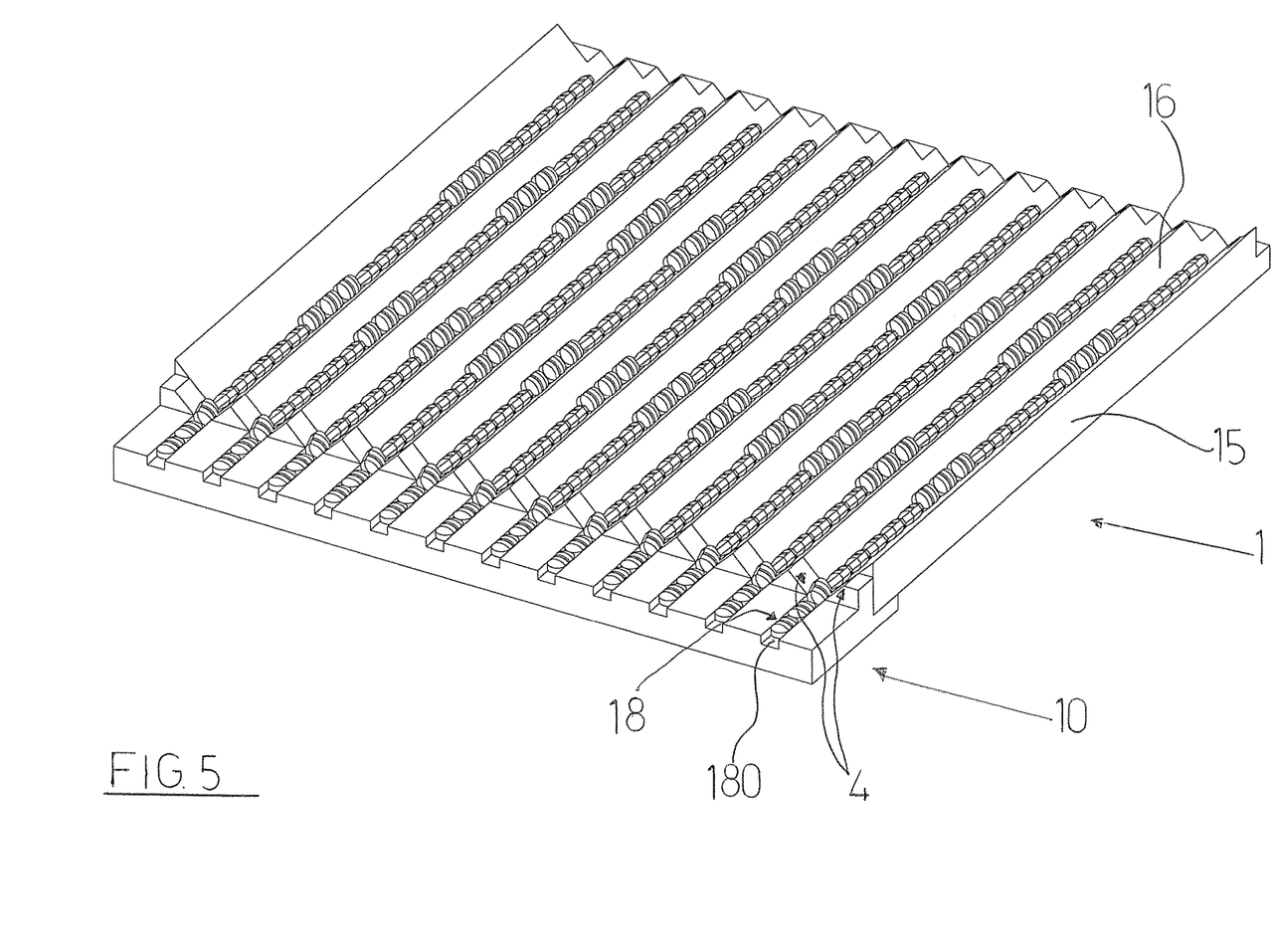
FIG. 5 is a schematic perspective view of a particularly important component of the system of the invention according to the embodiment of FIG. 4.

In the preferred embodiment illustrated in the figures, see for example FIG. 4 and FIG. 5, the vibrating conveyor (15) comprises twelve V-shaped channels (16) and relative twelve straight channels (18), each of which is arranged consecutively to a corresponding V-shaped channel (16).

In this case the system (S) comprises four video colour matrix cameras (2), each of which is arranged so that the relative visual field (V1) contemporaneously involves three corresponding straight channels (18) of the vibrating conveyor (15), so as to capture the images of the articles which advance in a line in each of the three channels (see FIG. 4).

In turn, the laser projector (P) is predisposed so that the laser beam (L) crosses all twelve straight channels (18) in a position below the visual field (V1) of each of the four colour matrix video cameras (2) while the high-speed linear three-dimensional video camera (3) is arranged such that the relative visual field (V2) for capturing the images involves all twelve straight channels (18) at the position in which the laser beam (L) crosses the twelve straight channels (18) internally of the visual field (V1) for capturing the images of the four colour matrix video cameras (2).

In a possible further embodiment, not illustrated in the figures, the system (S) can be provided with means for carrying out an overturning of the articles in advancement along the advancement section (10) after they have exited from the visual field (V1) of the colour matrix video camera (2), so as to arrange the articles still flat but resting on the advancement section with another face thereof, and consequently including a further laser projector which projects a laser beam so that it crosses the advancement section in a position downstream of the point in which the articles are overturned, so that the overturned articles cross the laser beam.

In this case the system will have at least a further colour matrix video camera for capturing images of the outline and the colour of the overturned articles and a further high-speed three-dimensional linear video camera for capturing the images of the profiles cut in the laser beam by the overturned articles.

In this way the processor will also have the images of the overturned articles available and therefore will possess more information for processing the final datum on the effective integrity and suitability thereof.

The invention claimed is:

1. A detection system for detecting and determining an integrity of pharmaceutical/parapharmaceutical articles, comprising:

a conveyor device, for conveying and advancing articles, the conveyor device comprising an advancement section in which the articles are advanced on a flat plane, in a line one after another in an advancement direction;

a processor for data processing;

at least a colour matrix video camera connected to the processor and arranged above the advancement section of the conveyor device and arranged so that a lens thereof is facing towards the advancement section so that a visual field thereof for capturing images is at the advancement section, along which the articles are advanced in a line, one after another, so that the colour matrix video camera can capture a series of images of an outline and a colour of each article, during the advancement thereof along the advancement section across the visual field of the colour matrix video camera, the processor being programmed to receive the images captured by the colour matrix video camera and to process the images so as to supply, for each article, a first datum relative to an effective shape of the outline and colour of the article;

a laser projector able to emit and project a laser beam, the laser projector being positioned above the conveyor device and predisposed such as to project and direct a laser beam into the advancement section of the articles in a position internally of the visual field of image capture of the at least a colour matrix video camera, in such a way that the laser beam can be crossed by each of the articles advancing in a line one after another along the advancement section;

a high-speed linear three-dimensional video camera connected to the processor and predisposed so that a lens thereof is facing towards the advancement section so that a visual field thereof for capturing images is at a zone in which the laser beam is crossed by the articles advancing in a line, one after another, along the advancement section, internally of the visual capturing field of the at least a colour matrix video camera, such that the high-speed linear three-dimensional video camera can capture a succession of images corresponding to successive outlines cut in the laser beam by each article as it crosses the laser beam, the processor being further programmed so as:

to receive the images of the successive profiles cut in the laser beam by each article, captured by the high-speed linear three-dimensional video camera;

to process the images, captured by the high-speed linear three-dimensional video camera, so as to supply a second datum relating to the effective thickness and shape of the three-dimensional profile of each article which has crossed the laser beam;

to associate the second datum to the first datum concerning the outline and colour of the same article;

to process the first datum and the second datum so as to define, for each article which is transited from the advancement section and which has crossed the laser beam, an indicative datum of the outline, colour, thickness and three-dimensional profile of the article;

to compare the indicative datum with a reference datum representative of a whole article having a predetermined outline, colour, thickness and three-dimensional profile, and consequently supply a validation or rejection notice in relation to the article.

2. The system of claim 1, wherein the at least a colour matrix video camera is arranged above the advancement section so that an axis of the respective lens is perpendicular to the plane of the advancement section, in that the laser projector is arranged such that the laser beam crosses the plane of the advancement section at an angle between 90° and 40°, and in that the high-speed linear three-dimensional video camera is arranged such that the axis of the respective lens forms, with the plane of the advancement section, an angle between 60° and 20°.

3. The system of claim 1, wherein the at least a colour matrix video camera is a video camera having a resolution of 1280×1024 pixels, in that the high-speed linear three-dimensional video camera is a video camera known as a "high speed 3D camera" with a resolution of 2048×1088 pixels which supplies to the processor a profile at 2048 heights on the basis of the profile cut in the laser beam by the passage of an article.

4. The system of claim 1, wherein the conveyor device comprises a vibrating conveyor comprising at least a V-shaped conveyor channel along which the articles are advanced in an inclined configuration resting on one of two walls of the V-shaped conveyor channel, and in that the advancement section is constituted by at least a straight channel which is arranged consecutively to the V-shaped conveyor channel and in that it exhibits a flat bottom on which the articles rest and walls conformed in such as way as to be able to receive and accommodate the articles so that the articles are arranged with a face thereof resting on the flat bottom, and in that the vibrating conveyor comprises switching and orientating means for orientating and arranged the articles in outlet from the V-shaped conveyor channel resting with a face thereof on the flat bottom of the straight channel.

5. The system of claim 4, wherein the vibrating conveyor comprises twelve V-shaped channels and respective twelve straight channels each of which is arranged consecutively to a corresponding V-shaped channel and comprises four colour matrix video cameras, each of which is arranged so that the respective visual field involves three corresponding straight channels of the vibrating conveyor so as to capture images of the articles which advance in a line in each of the three channels, in that the laser projector is predisposed so that the laser beam crosses all twelve straight channels in a position below the respective visual fields of the four colour matrix video cameras and in that the high-speed linear three-dimensional video camera is arranged such that the respective visual field for capturing the images involves all twelve straight channels at the position in which the laser beam crosses the twelve straight channels.

* * * * *